United States Patent [19]

Lakatos

[11] Patent Number: 4,620,972

[45] Date of Patent: Nov. 4, 1986

[54] METHOD OF INHIBITING THE GROWTH OF MALIGNANT TUMOR CELLS

[76] Inventor: George C. Lakatos, 29260 Franklin, Southfield, Mich. 48034

[21] Appl. No.: 881,467

[22] Filed: Feb. 27, 1978

[51] Int. Cl.[4] ...................... A61K 43/00; A61K 49/00
[52] U.S. Cl. .......................................... 424/1.1; 424/9
[58] Field of Search .......................... 424/1, 1.5, 9, 1.1

[56] References Cited

U.S. PATENT DOCUMENTS 4,132,769  1/1979  Osther ..................................... 424/1

OTHER PUBLICATIONS

Gregory et al, Biochimica Etbiophysica Acta, vol. 130, No. 2, Dec. 28, 1966, pp. 469-476.

Ng et al, Biochem. Biophys. Acta, vol. 130, No. 2, Dec. 28, 1966, pp. 477-485.

Ng et al, Biochem. Biophys. Acta, vol. 170, No. 1, Nov. 12, 1968, pp. 45-53.

*Primary Examiner*—Christine M. Nucker
*Attorney, Agent, or Firm*—Jay C. Taylor; Neal A. Waldrop

[57] ABSTRACT

There is provided a method of inhibiting the development of human cancer cells by parenterally administering to human cancer patients lactate dehydrogenase obtained from a primate or anti-lactate dehydrogenase obtained from a mammal as a result of the parenteral administration of primate lactate dehydrogenase to said mammal, thus inhibiting the lactate dehydrogenase activity in the human cancer cells.

10 Claims, No Drawings

METHOD OF INHIBITING THE GROWTH OF MALIGNANT TUMOR CELLS

BRIEF DESCRIPTION OF THE INVENTION

This invention relates to a method of inhibiting the development of malignant tumor cells and more particularly to a process which produces remission of cancer in human being by means of antibodies created by lactate dehydrogenase from a primate.

DETAILED DESCRIPTION OF THE INVENTION

In the past most attempts to discover a cure for cancer have involved research directed toward identifying the cause or causes of the malignancy, either generally or specifically. Hence a broad range of carcinogenic agents has been partially identified. However, very little effective work has been done previously in the area of identifying and inhibiting the basic biochemical reactions involved in the development of malignant neoplasms and metastasis.

Accordingly, a principal object of the present invention is to provide a method of inhibiting the development of cancer cells in human beings by restricting the biochemical reaction within these cells in a manner which prevents the spread of the neoplasm and results in necrosis of the cancerous tissue. This object is obtained in accordance with this invention by a process in which lactate dehydrogenase is obtained from a primate and parenterally administered to the human cancer patient to stimulate the production in the patient of antibodies (anti-lactate dehydrogenase) which inhibit the action of the lactate dehydrogenase in the malignant tumor cells of the patient. The biochemical mechanism involved and variations of the basic procedure are described in greater detail below.

Cancer can be induced by a great range of agents, including chemical carcinogenesis, oncogenic viruses and physical carcinogenesis, such as ionizing radiation. Because of their diversity it is certain these agents must specifically operate by different biochemical routes. However, it appears that these routes lead to a key alteration similar in principle in the different cases, notwithstanding the great diversities between the carcinogens themselves or even between many of the oncogenic viruses.

As has been well known for several decades, the metabolism of malignant tumor cells in the human body and other animal life is different from that of normal cells. A normal cell utilizes both glycolysis and the tricarboxylic acid cycle, the latter requiring the presence of oxygen and produces water and carbon dioxide in the metabolic process. Cancer cells, on the other hand, are largely anaerobic. The energy for the rapid and normally uncontrollable growth of a malignant tumor cell therefore results from glycolysis, the chemical reactions in which glucose is converted to lactic acid. However, the presence of the enzyme lactate dehydrogenase or lactic acid dehydrogenase (hereinafter usually referred to as LDH in accordance with conventional usage) is essential for the completion of the reactions and the production of lactic acid. The LDH functions as a catalyst, and lactic acid will not be produced in the absence of this enzyme.

All energy production in mammalian tissue involves two metabolic pathways. One is the glycolytic cycle, the enzymes for which reside in the cell cytoplasm, and the other is the tricarboxylic acid cycle whose enzymes are organized within the cell mitochondria. Under normal conditions glycolysis proceeds in the cytoplasm of the cell to the pyruvate stage. The pyruvate produced is then fed, via acetyl coenzyme A., into the tricarboxylic acid cycle, while the resultant reduced form, nicotinamide adenine dinucleotide (NADH), is reoxidized via the electron transport chain, also within the mitochondria.

In the event the mitochondrial mechanisms are not available, pyruvate may be reduced to lactate in the cytosol, thus reoxidizing the NADH formed earlier in the glycolytic cycle. This reaction is mediated by lactate dehydrogenase. Many cancer cells, for reasons not fully understood at the present time, are dependant on glycolysis, rather than on the tricarboxylic acid cycle and the associated electron transport chain, for their energy production. I have found that these cancer cells may be destroyed by inhibiting the LDH-mediated step of glycolysis because the vital coenzyme, nicotinamide adenine dinucleotide in oxidized form, will be rapidly depleted. The anaerobic energy-yielding conversion of glucose to lactic acid thus is not completed since the reaction appears to be halted at the pyruvic acid stage.

In accordance with one procedure involved in the present invention, the human cancer patient is immunized with a foreign LDH obtained from another primate, preferably monkeys and the family Pongidae. The patient responds by producing antibodies to the foreign LDH. The LDH obtained from the higher primates, while functionally "recognized" as a foreign protein by the cancer host, is structurally sufficiently similar to the human LDH so that the antibody (anti-LDH) formed can cross-react with the human LDH, thus inhibiting the human cancer LDH activity and thereby destroying the cancer cells.

In some instances it appears desirable to treat patients by passive rather than active immunization because frequently the human cancer patient is incapable of producing the necessary antibodies. Therefore, passive immunization is indicated in instances where the patient is severely debilitated.

In a preferred embodiment of the process of the present invention, an anti-LDH derived from another human being or other primate is administered to the cancer patient rather than injecting primate LDH. The anti-LDH is "raised" in the primate, the primate thereafter bled, and the anti-LDH in said blood isolated from other plasma proteins by chromatography. A usable variation of this procedure involves obtaining LDH from a rhesus monkey, for example, injecting it into another primate to develop antibodies, and injecting the anti-LDH so obtained into the human cancer patient.

This process also can utilize a transfer mechanism in which the anti-LDH produced in a healthy human body, for example, are made radioactive and then introduced parenterally into the body of the patient to destroy the cancer cells by radioactive means. The anti-LDH can be associated with an energetic, short-lived radionuclide for this purpose, the anti-LDH functioning as the delivery vehicle for the radionuclide. Such a radionuclide can be attached to a protein such as the anti-LDH by the Hunter Greenwood procedure. Alternatively, it is possible to use the aforesaid transfer mechanism by producing the anti-LDH in the body of the cancer patient and reintroducing this anti-LDH into the patient's body parenterally.

In accordance with the principles involved in the present invention, it has been recognized that malignant tumor tissue breaks down glucose to lactic acid at a far greater rate then does normal tissue. Hence cancer cells have significantly greater susceptibility to inhibition by the anti-LDH than do normal cells, making the use of LDH in the process of this invention especially effective. Moreover, immunological regimens such as that involved in the present invention can reach the very last cancer cell. This action is in contrast to most chemotherapeutical regimens which are effective in reducing the number of cells in a malignant tumor but evidence an inability to affect every such cell. Also of clinical importance is the fact that the administered agent, LDH, is non-toxic. Furthermore, in the event a cancer patient who was previously treated in accordance with the process of the present invention subsequently develops a new cancer, even one of a different type, treatment is simplified because the injection of LDH or anti-LDH from the source previously employed produces an amnestic response which is characteristic of immunological responses. This reaction, in turn, indicates the potential practical applicability of the inventive concept as a vaccination procedure. There is no reason why the LDH process described herein cannot be used in conjunction with chemotherapy, surgery, radioisotope therapy and perhaps other forms of immunotherapy.

The LDH may be obtained from a rhesus monkey, for example, or other desired primate by standard procedures such as those described on pages 441–443 of the article by Arthur Kornberg entitled "Lactic Dehydrogenase of Muscle" which appeared in *Methods of Enzymology*, Vol. I, Ed: Colowick Kaplan. Academic Press, 1955.

Purification of the antibodies produced can be achieved by standard chromatographic procedures, such as affinity chromatography or ion exchange chromatography. The purified material is then dialyzed and subsequently lyophilized for storage purposes. When it is to be employed in passive immunization, the lyophilized material is thereafter redissolved in water.

The most pertinent prior art of which I am aware is that disclosed in a publication of which I am co-author, "Prolonged Remissions of Lymphatic Leukemia in DBA/2 Mice Induced with Endogenously Produced Lactate Dehydrogenase Antibody", by G. Lakatos, A. Stiefling, R. R. Joseph and D. S. McCann, Cancer Research 34:1395, June 1974. Also of interest are the following prior publications:

Lakatos, G., Der Einfluss von Milchsauere Dehydrogenase auf Malignes Tumorgewebe, Inaugural Dissertation, Univ. Bern, Switzerland, 1956;

Gregory, K. F., Mg. C. W. and Pantekoek, J. F., Antibody to Lactate Dehydrogenase, I. Inhibition of Glycolysis in Tumor and Liver Homogenates, Biochim. Biophys. Acta, 130:469, 1966;

Ng, C. W. and Gregory, K. F., Antibody to Lactate Dehydrogenase, II. Inhibition of Glycolysis and Growth of Tumor Cells, Biochim. Biophys. Acta, 130:477, 1966; and Ng, C. W. and Gregory, K. F., Antibody to Lactate Dehydrogenase, III. Uptake, Accumulation and Specific Intracellular Action in Malignant Cells, Biochim. Biophys. Acta, 170:45, 1968.

While the present invention has been described by means of certain specific examples, it should be understood that additional variations of the procedures embodying the inventive concept are possible and that the scope of the invention is set forth in the following claims.

What I claim is:

1. The method of selectively inhibiting the metabolism of cancer cells in a human cancer patient, comprising the provision in the patient of antibodies to a foreign lactate dehydrogenase (LDH) which is capable when injected parenterally into a patient of stimulating the production of said antibodies in the patient and structured so that the antibodies thus produced will cross react effectively with the LDH of the patient's cancer cells to inhibit LDH mediated glycolyis in the cancer cells.

2. The method according to claim 1 wherein the foreign LDH is obtained from a primate and is introduced parenterally into the patient to stimulate the production of the antibodies in the patient, and wherein the cancer cells are selectively starved by the antibody action.

3. The method according to claim 1 wherein the antibodies are extracted from the patient, rendered radioactive, and thereafter reintroduced parenterally into the patient to carry radioactivity into the cancer cells.

4. The method according to claim 1 wherein the foreign LDH is obtained from a primate and is injected parentally into a mammal to stimulate the production of the antibodies which are then extracted from the mammal and injected parenterally into the patient.

5. The method according to claim 4 wherein the antibodies from the mammal are made radioactive and thereafter introduced parenterally into the patient for subsequent entry into the cancer cells.

6. The method of inhibiting the development of cancer set forth in claim 1 in which the lactate dehydrogenase is extracted from the muscle of a primate selected from the group consisting of homo sapiens, monkeys and the family Pongidae.

7. The method of inhibiting the developmnent of cancer set forth in claim 4 in which the mammal into which the lactate dehydrogenase is introduced is a primate.

8. A method of inhibiting human cancer cell growth comprising:
    obtaining lactate dehydrogenase from a primate, injecting said lactate dehydrogenase into the body of a second primate to produce anti-lactate dehydrogenase,
    thereafter drawing blood from said second primate,
    subsequently separating by chromatography the anti-lactate dehydrogenase in said blood from other plasma proteins therein, and injecting said anti-lactate dehydrogenase thus produced into the body of the human cancer patient in a quantity sufficient to inhibit the lactate dehydrogenase activity in the human cancer cells.

9. A method of inhibiting the growth of cancer in a human patient comprising:
    obtaining anti-lactate dehydrogenase from a human body,
    treating the anti-lactate dehydrogenase so obtained to make it radioactive, and
    thereafter parenterally introducing said radioactive anti-lactate dehydrogenase into the body of the cancer patient in a quantity sufficient to destroy the cancer cells by radioactive means.

10. The method of inhibiting the growth of cancer in a human patient set forth in claim 9 in which the anti-lactate dehydrogenase is associated with an energetic short-lived radionuclide.

* * * * *